US011857405B2

(12) United States Patent
Rauchfuss et al.

(10) Patent No.: US 11,857,405 B2
(45) Date of Patent: Jan. 2, 2024

(54) MEDICAL IMPLANT BASED ON NANOCELLULOSE

(71) Applicants: Universitätsklinikum Jena, Jena (DE); KKF UG, Jena (DE)

(72) Inventors: Falk Rauchfuss, Jena (DE); Utz Settmacher, Jena (DE); Dieter Klemm, Weimar (DE); Wolfgang Fried, Jena (DE); Thomas Richter, Jena (DE); Katrin Petzold-Welcke, Bad Sulza OT Wickerstedt (DE); Carola Ruhe, Dessau (DE)

(73) Assignee: Universitätsklinikum Jena, Jena (DE)

( * ) Notice: Subject to any disclaimer, the term of this patent is extended or adjusted under 35 U.S.C. 154(b) by 0 days.

(21) Appl. No.: 17/526,521

(22) Filed: Nov. 15, 2021

(65) Prior Publication Data
US 2022/0071758 A1     Mar. 10, 2022

Related U.S. Application Data

(62) Division of application No. 15/749,563, filed as application No. PCT/EP2016/068580 on Aug. 3, 2016, now abandoned.

(30) Foreign Application Priority Data

Aug. 5, 2015 (EP) .................................. 15179884

(51) Int. Cl.
*A61F 2/04* (2013.01)
*A61L 31/14* (2006.01)
(Continued)

(52) U.S. Cl.
CPC .............. *A61F 2/04* (2013.01); *A61L 31/005* (2013.01); *A61L 31/10* (2013.01); *A61L 31/146* (2013.01);
(Continued)

(58) Field of Classification Search
CPC ......... A61F 2/04–2002/068; A61F 2210/0076; A61F 2210/0004; A61F 2240/001;
(Continued)

(56) References Cited

U.S. PATENT DOCUMENTS 5,609,629 A      3/1997  Fearnot et al.
10,709,821 B2 *  7/2020  Ulmer ..................... A61F 2/062
(Continued)

FOREIGN PATENT DOCUMENTS

CN     101474424 A      7/2009
EP     0396344 A1      11/1990
(Continued)

OTHER PUBLICATIONS

Office Action dated May 27, 2022 by the Canadian IPO in the corresponding Patent Application No. 2,993,374.

*Primary Examiner* — Paul B Prebilic
(74) *Attorney, Agent, or Firm* — Norton Rose Fulbright US LLP; James R. Crawford

(57) ABSTRACT

Medical Implant (100), comprising
  a microbial cellulose tube (1), comprising a wall (2) having an inner surface (3) and an outer surface (4), wherein the wall comprises several layers (5, 6, 7) of microbial cellulose, wherein said layers are concentric or substantially concentric to a longitudinal axis (L) of the tube,
  a stent (9) which placed inside of the microbial cellulose tube (1), wherein an outer surface (10) of the stent contacts the inner surface (3) of the microbial cellulose tube (1), and method for producing such implant.
The implant can be covered with newly created bile duct epithelium, thereby creating a new bile duct from body cells. The implant can be removed after completion of creation of the new bile duct. So, the implant as suitable as a temporary implant.

(Continued)

Figure 1:
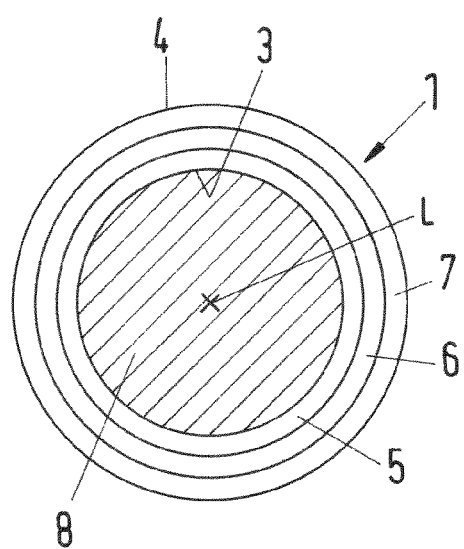

The implant can be used for surgery, such as surgery of gall bladder, bile duct and/or liver, e.g. gall bladder removal, hepatobiliary malignancy surgery or liver transplantation. The implant can particularly be used for repairing or regeneration of bile duct. Further fields of use are the use as esophagus implant or urether implant.

25 Claims, 3 Drawing Sheets

(51) Int. Cl.
  *A61L 31/10* (2006.01)
  *A61L 31/00* (2006.01)
  *C08L 1/02* (2006.01)
(52) U.S. Cl.
  CPC ..... *A61F 2002/041* (2013.01); *A61L 2400/12* (2013.01); *A61L 2420/08* (2013.01); *C08L 1/02* (2013.01)
(58) Field of Classification Search
  CPC ......... A61F 2250/0039; A61L 2420/02; A61L 2420/08; A61L 2430/22; C08L 1/02; C08L 2203/02

See application file for complete search history.

(56) References Cited

U.S. PATENT DOCUMENTS

| | | |
|---|---|---|
| 2003/0013163 A1 | 1/2003 | Klemm et al. |
| 2003/0138950 A1 | 7/2003 | McAlliser et al. |
| 2006/0122695 A1 | 6/2006 | Atala |
| 2006/0147612 A1 | 7/2006 | Da Rocha Loures |
| 2012/0330402 A1 | 12/2012 | Vad et al. |
| 2014/0277354 A1* | 9/2014 | Allain .................... A61L 31/16 623/1.11 |

FOREIGN PATENT DOCUMENTS

| | | |
|---|---|---|
| WO | 2013056049 A2 | 4/2013 |
| WO | 2013113675 A1 | 8/2013 |

* cited by examiner

MEDICAL IMPLANT BASED ON NANOCELLULOSE

CROSS REFERENCE TO RELATED APPLICATIONS

The present application is a divisional application of U.S. patent application Ser. No. 15/749,563, filed on Feb. 1, 2018, now abandoned, which is a U.S. National Phase of International Application PCT/EP2016/068580, filed on Aug. 3, 2016, and claims the benefit under 35 U.S.C. § 119 of European Patent Application No. 15179884.0, filed on Aug. 5, 2015, each of which is hereby incorporated by reference in its entirety.

The present invention relates to a medical implant, particularly for repairing a bile duct, and a method for producing such implant.

In hepato-biliary surgery a reconstruction of the biliary duct is often a critical issue since loss of biliary duct substance often forces the surgeon to high-risk operations or to operations like bilioenteric anastomosis. Such loss of substance, or lesions, may happen when gall bladder is removed and the common bile duct is incidentally injured or when damages are caused by ischemia, e.g. after liver transplantation or tumor resection.

Reconstruction of such lesions is complicated. In most cases a so called "bilioenteric anastomosis" has to be performed, which is a connection between common bile duct and parts of the gastrointestinal tract. In this procedure, an intestinal loop is connected to the common bile duct. The basic problem of this method is that sphincter mechanism is bypassed, which is the natural barrier between biliary system and intestinal lumen.

This often results in migration of intestinal bacteria in the bile duct, which can lead to an infection of the biliary system. Particularly patients after a liver transplantation are affected by this problem and endangered due to their immunosuppressed state.

Attempts to eliminate a bile duct defect are known from only a few scientific groups. Aikawa et al (2012) describe a bile duct replacement by implantation of a polymeric tube that could be resorbed. A histologic evidence of a completely regenerated bile duct could be made no earlier than after four months, which is a too long time for a successful application in human body. Moreover, it is difficult to coordinate the new formation of bile duct and resorption of the polymer tube, particularly when taking into consideration the specific constitution and situation of an individual patient. The same problems occur when the technique published by Palmes et al. (2009) is used. Here, implantation of an autologous segment of a vein (external jugular vein) was implanted and stabilized with an absorbable or resorbable stent. With this method, it took even six months for creating a new bile duct. Moreover, not every patient possesses suitable veins and a further surgical intervention is necessary in order to obtain the necessary vein segment.

The present invention is based on the problem of providing an improved medical implant, particularly for repairing a defect in a bile duct. Particularly, it was an object to provide a material for bile, bile duct and liver surgery that is able to fulfil one or more of the following tasks:

- to bypass or bridge a defect in a bile duct, preferably also over a long distance;
- to enable a reconstruction of a bile duct, without using a connection between bile or bile duct and parts of the gastro-intestinal tract;
- to induce a regeneration of the bile duct epithelium.

One or more of the above objects are obtained with the present invention. The present invention provides with a medical implant and a method for producing such implant as stated in the independent claims.

It has been shown that with the present invention, in general or in specific embodiments, one or more of the following benefits are obtained:

- A new bile duct from body's own tissue could be created on the implant. Bile duct epithelium is created on the implant. The implant creates a stimulus for regeneration of body tissue, at least as far as a bile duct is concerned. Defects in a bile duct can thus be repaired by using the implant of the invention. Sufficient anastomosis can be reached.
- The implant of the invention easily be produced. Diameter, length and especially structure and properties of the inner and outer surface of the tube can be designed directly in a bioreactor in view of the envisaged application or situation.
- It is possible to repair defects in a bile duct that extend over a longer distance. So, a sphincter mechanism can be retained and infections avoided.
- After regeneration of the bile duct, the implant can easily be removed. The nanocellulose does not form a firm connection to the newly created body tissue. No foreign matter remains in the organism.
- The implant can be used for permanent or temporary interposition.
- The nanocellulose tube of the implant can be used as interponate, particularly for a bile duct.
- In the invention it was surprisingly shown that in a living organism a non-degradable artificial implant was covered with newly created bile duct epithelium, thereby creating a new bile duct from body cells. Nevertheless, the implant can be removed after completion of creation of the new bile duct. So, the implant is suitable as a temporary implant.

The present invention particularly provides with a medical Implant, comprising a microbial cellulose tube, comprising a wall having an inner surface and an outer surface, wherein the wall comprises multiple layers of microbial cellulose, wherein said layers are concentric or substantially concentric to a longitudinal axis of the tube, a stent which is placed inside of the tube of microbial cellulose.

In the implant, the microbial cellulose tube surrounds the stent.

In one embodiment, an outer surface of the stent contacts the inner surface of the microbial cellulose tube. In this embodiment, the microbial cellulose tube is placed on the outer surface of the stent.

The medical implant of the invention is preferably used as a temporary medical implant which can be completely or partially removed after having fulfilled its function. In partial removal, the stent is removed from the body. When completely removed, also the tube is removed. For clinical application, the tube and the stent can be removed via an endoscopic approach. In our experiments the regenerated bile duct was stable. Thus, all or nearly all "foreign material" will be removed out of the biliary system.

According to a basic principle of the invention the microbial cellulose tube is not the intended replacement for a bile duct. Instead, the microbial cellulose tube is a support for growth of a new bile duct, or bile duct segment from body's own tissue. The implant of the invention is particularly suitable for generating a new bile duct from body's own tissue, or for repairing a bile duct by generating a new bile duct section from body's own tissue between two already existing bile duct ends.

When using the implant, and at the end of use, body tissue grows/has been grown on the surface of the microbial cellulose tube and so, a bile duct can be created or repaired.

The stent is introduced into the microbial cellulose tube (also abbreviated as "tube"), i.e. into the interior, also called the cavity, of the tube. The stent keeps open the interior, or the lumen, of the tube and prevents a closure of the tube. A stent can lead to expansion of the tube, as described below, and thereby improve the functionality of the implant. Preferably, the stent is slit into the microbial cellulose tube. The microbial cellulose tube surrounds the stent.

In one embodiment, the stent is a tubular stent. The term tubular stent also comprises stents having one or more openings on the surface or the jacket of the tube. The tubular stent can comprise a tube made of a mesh structure or a tube with closed jacket.

The outer diameter of the stent may be the same, smaller, or higher, particularly slightly higher, than the inner diameter of the microbial cellulose tube. If the outer diameter of the stent is higher, the tube is expanded. The implant may comprise an expanded microbial cellulose tube, preferably expanded in radial direction. Expansion means an expansion in comparison to a tube that is not combined with the stent. The inner diameter of the cellulose tube is the inner diameter of the tube before it is combined with the stent.

A stent is a hollow device placed in the body and may be used to create a passage between two hollow spaces or for keeping open a hollow organ or a vessel. In the present invention the stent is used as stiff support for the microbial cellulose tube. In this sense, the stent is used for keeping open the microbial cellulose tube. The stent can also keep open parts of an existing duct in the body, for example parts of a bile duct.

The stent is preferably a billiary stent. The stent may be made of polymer, particularly it can be a polymer tube. The stent may comprise openings on its outer surface. Such openings can be openings that are present in addition to openings at both ends of a stent.

The stent can be over its whole length placed inside of the tube of microbial cellulose or over a part of its length placed inside of the tube. In one embodiment, the stent protrudes from the microbial cellulose tube at one end (a first end) of the microbial cellulose tube and an opposite end (a second end) of the microbial cellulose tube. A protrusion has the advantage that protruding ends of the stent can be inserted each into the bile duct, for example, when between two bile duct segments new tissue shall be generated in order to connect the segments. A protrusion means a protrusion in longitudinal direction, i.e. in direction of the longitudinal axis (L) of the tube.

In insertion of the implant can comprise following steps:
insertion of the stent, particularly protruding parts of the stent, into two bile duct segments,
placing the cellulose tube between the bile duct segments. Thereby, each edge of the both bile duct segments can be placed adjacent to an edge of the tube at the end of the tube, respectively. Each edge of a bile duct can be in contact to said edge of the tube.
optionally: connecting an end of the tube with a bile duct, preferably on both ends of the tube, by connection means. The connection means may be, for example, a suture.

After insertion of the implant, body tissue can grow over the tube until the bile duct segments are re-connected. Then, the implant can be removed.

In one embodiment, the outer layer of the bacterial nanocellulose LBNCI tube in the implant is subjected to pressure or strain, which can for example be done by expanding the BNC tube with a stent. It has been shown that by such measure, meshes are narrowed and a structure of BNC fibers in the outer layer is subjected to compaction. In one embodiment, a stent with an outer diameter larger than the inner diameter of the tube can be used, to reach this result. The inner diameter of the tube is the inner diameter of the tube before it is combined with the stent. By an expansion, at least the outer layer of the BNC tube is subjected to a compaction. Porosity of at least the outer layer of the tube is decreased. By such measure, better functionality of the implant could be observed, particularly a better disconnection from body tissue that has been formed on the outer layer. The implant of the invention may comprise an expanded microbial cellulose tube, preferably in radial direction. The term expanded means an expansion in comparison to a tube that is not combined with a stent, for example a tube after its production and optional storage in suitable liquid medium, such as deionized water.

In one embodiment, the microbial cellulose tube is expanded by the stent in radial direction. An expansion in radial direction means that at least the inner diameter of the tube is increased, and preferably that the inner and the outer diameter of the tube are increased. The expansion can be in one or more radial directions. The tube can be expanded in at least one radial direction, preferably in more radial directions, even more preferably in a multitude of radial directions or even each radial direction. The diameter can be increased in at least one radial direction, preferably in more radial directions, even more preferably in a multitude of radial directions or even each radial direction. The tube can be symmetrically or asymmetrically expanded, in relation to its longitudinal axis, or in relation to a distinct position or point at the longitudinal axis. The tube can be expanded in radial direction at one or more positions along the longitudinal axis of the tube, preferably a multitude of positions. Most preferably, the tube is radially expanded over most of its length or its whole length.

The tube and the stent may be linear or curved, or have one or more bends. A linear tube is also called hollow cylinder.

The following description is directed to the tube of microbial cellulose, its structure and methods for production. For these subject matters it is explicitly referred to patent application WO2013/113675A1 and its whole disclosure, which is incorporated by reference in this description.

The term "microbial cellulose" means a cellulose which is produced by a microorganism. Exemplary microorganisms are fungi, bacteria and algae. A number of microorganisms is able to produce microbial cellulose. These include, but are not limited to, algae such as Valonia and Boergesenia, fungi such as Dictyostelium discoideum and bacteria such as *Gluconacetobacter* (*Komagataeibacter*), *Enterobacter, Agrobacterium, Sarcina, Pseudomonas, Rhizobium* and *Zoogloea*. Examples of species *Acetobacter xylinum Gluconacetobacter, Acetobacter pasturianus, Acetobacter aceti, Acetobacter ransens*. A particularly useful microorganism is *Gluconacetobacter*, particularly *Gluconacetobacter xylinus*.

The layers of microbial cellulose in the tube are preferably made of a network of fibers.

Microbial cellulose may be produced by microorganisms at the interface between air and a nutrient medium in the form of a biofilm (fleece). The bacteria produce the cellulose in form of fibrils. These self-assemble into fibers. Through the interweaving of the fibers, a three-dimensional, highly hydrous nanofiber network of approximately 99% water and 1% cellulose is created (Jonas R, Farah L F: Production and application of microbial cellulose., Polym. Degrad. Staff (1998), 59 (1-3), 101-106; A Hirai, *Horii* F: Cellulose Assemblies produced by *Acetobacter xylinum*. ICR Annual Report (1999) 6, 28-29; Terminal D, Heublein B, Fink HP, Bohn A: Cellulose: Fascinating Biopolymer as sustainable raw material, Angew. Chem. Int. Ed. (2005) 44, 3358-3393).

Microbial cellulose is, if it is produced by bacteria, also named herein as "bacterial cellulose", "bacterial nanocellulose" (BNC) or simply "nanocellulose". The term "bacterial nanocellulose" is derived from the fact that bacterially produced cellulose, as mentioned above, forms a nanofiber network.

In one embodiment, the microbial cellulose tube, comprising several layers of microbial cellulose is obtainable by or obtained by a method comprising following steps:
  a) contacting the surface of a template which is a negative mold of a cavity of the microbial cellulose tube and of the inner walls of the cavity, with a stock mixture comprising a liquid culture medium and a cellulose-producing microorganism,
  b) interrupting of the contact between the template and the stock mixture, wherein on the surface of the template, a liquid film remains comprising the liquid culture medium and the microorganism
  c) contacting of the liquid film with an oxygen-containing atmosphere and formation of microbial cellulose in and/or on the liquid film,
  d) contacting the microbial cellulose obtained in step c) with the stock mixture,
  e) interrupting the contact between the microbial cellulose and the stock mixture wherein on the surface of the microbial cellulose is a film of liquid is left, which comprises the liquid culture medium and the microorganism,
  f) contacting the liquid film with an oxygen-containing atmosphere and formation of microbial cellulose in and/or on the liquid film, wherein the sequence of steps d), e) and f) is repeated one or more times,
  g) separating the microbial cellulose from the template.

With this method, a tube composed of multiple distinct layers of microbial cellulose can be produced.

In one embodiment, the microbial cellulose tube, singly or as part of an implant of the invention, can show one or more of features, singly or in any combination:
  a length of 10-200 mm, preferably 20-180 mm, more preferably 50-150 mm,
  an inner diameter of 2-10 mm, preferably 2-8 mm,
  an outer diameter of 3-15 mm, preferably 4-10 mm,
  a wall thickness of 1-5 mm, preferably 1-3 mm,
  a number of distinct BNC layers of 3-10, preferably 5-10.

The culture medium, also referred to as a "broth" or "broth" may contain conventional ingredients for culturing a cellulose producing microorganism such as glucose, peptone, yeast extract, sodium hydrogen phosphate and citric acid in aqueous solution (Hestrin Schramm medium). An alternative acidic medium consists of an aqueous solution of glucose, peptone, yeast, acetic acid and ethanol.

The method is preferably carried out at a temperature of 20 to 40° C.

In the method for producing the tube cultivation is carried out not purely static. The template and stock mixture containing culture solution and microorganism are moved relative to each other so that the surface of the template is wetted. A permanent contact of the template with the mixture stock is excluded. The template and the mixture reservoir, having the culture medium and the microorganism can be moved relative to each other, thereby temporarily, but not permanently brought into contact. Feature of the method is a template that is periodically, but not permanently, brought into contact with culture solution and microorganism, the formation of a film containing the culture medium and the microorganism on the template and the biosynthesis of cellulose in the template only in and/or on the film—outside of the stock mixture.

The term "interrupting contact" means that the contact between the template and mixture stock is so interrupting that no part of the surface of the template during the interruption has contact with the mixture stock.

In the method, the shape of the interior, or the inner contour, of the tube is defined by a suitably shaped template, on whose surface in carrying out the method, a liquid film is formed, in which the biosynthesis of cellulose happens. Thus, the cellulose produced directly on the template surface later forms the inner surface of the tube. A first layer of cellulose is formed on the template. Further layers are formed by steps d), e), f) and their repetition. Steps b) and c) can be a combined step. Steps e) and f) can be a combined step. The outer shaping of the hollow body according to the invention is carried out without contact, only through the influence of gravity. After wetting process, the wetted template is free in the surrounding oxygen-containing atmosphere and the cellulose-forming process is performed in and/or on the film. The outer shape of the hollow body is defined solely by the choice of culture conditions. The culture conditions include, for example, the direction of the force of gravity, the frequency and spacing of individual turns, the time interval between the wetting time, the residence time, as explained below, the temperature and the cultivation time.

The method for producing the tube can be carried out in the apparatus described in WO2013/113675A1.

BNC-tubes produced by the method are characterized by improved mechanical properties and bioactive surfaces. So, on a bioactive outer surface body tissue, particularly bile duct epithelium can be generated.

Length and internal diameter of the tube are variable and variably combined. Exemplary internal diameters are 1-30 mm, preferably 2-8 mm, and exemplary lengths are 5 to 500 mm, preferably 100-200 mm. The length to diameter ratio is preferably greater than 1. The inner diameter can also vary within a tube.

The tube, particularly its cavity, may also have a differently shaped cross-section, for example a square, rectangular, triangular or star-shaped cross-section instead of a round.

The template is, as already mentioned, the negative mold of the cavity of the tube and the inner wall of the tube. The term "negative mold" refers to the tool, the male mold is the desired result, in this case, the tube/void/tube wall. The template is shaped complementary to the shape of the desired cavity produced and is specified accordingly. Accordingly, the shape of the template is defined by the shape of the above-mentioned hollow body. The template sets the internal geometry of the hollow body. For example, the template is cylindrical, with a diameter of 1-30 mm, preferably 2-8 mm, and a length of 5-500 mm, preferably 100-200 mm. As the tube cavity, the template may have an arbitrary cross-section, such as round, rectangular, in particular square, rectangular, triangular, or star-shaped or snowflake-shaped.

In one embodiment, the template has a surface having the structures in the millimeter, micrometer and/or nanometer scale. The structures are, for example, protrusions or depressions or both. The structures may have different geometries.

The material from which the surface of the template is made from is in principle not limited. In one embodiment, the template has a surface made of wood, metal, such as aluminum, stainless steel or titanium, plastics, ceramics, synthetic polymers such as polypropylene, polyesters, polyamides or Teflon, paper or glass fabric. The template material can be used pure or surface-coated in a proper manner. It can also be the entire template from one of the mentioned substances exist.

In a specific embodiment, an arrangement of a plurality of templates is employed in the process, also referred to as template matrix. It can templates with the same or different geometry, in particular different cross-sections, and/or be used of the same or different material. Thereby several identical or different tubes can be obtained in the method. An example of an arrangement of a plurality of templates is an arrangement of a plurality of cylindrical templates for the production of several tubes. Multiple templates of the same or different geometry can be fixed in a jig (template array).

In the method the template is periodically, preferably for a short time, wetted with the mixture comprising the culture broth and the microorganism. Here, a liquid film forms on the surface of the template. The shape of this liquid film is determined by the position of the template in the room, because the gravity acts on this film.

On the surface of the template, a liquid film is formed, comprising the liquid culture medium and the microorganism. In and/or on the liquid film microbial cellulose is formed. The liquid film can be distributed on the template by the template is rotated about one or more spatial axes, for example X, Y and/or Z in a Cartesian coordinate system. This is explained in the examples of WO2013/113675A1 by means of the movement device. By a predetermined movement of the template even better distribution of the liquid is achieved on the surface of the template. The distribution of the liquid can be influenced by the type of the predetermined rotational movement of the template, wherein the rotational movement can also be interrupted. The external geometry of the tube is thus determined by a defined distribution of liquid film and by a defined movement under the influence of gravity.

Preferably, the template has a geometry with a length to diameter ratio of greater than 1. For example, the template may have a cylindrical geometry with a length to diameter ratio of greater than 1, for producing a straight tube. The template has a longitudinal axis. In particular, the tube is a hollow cylinder with a central axis which runs centrally and longitudinally of the cylinder expansion through the cavity. The process is then preferably carried out so that the template is rotated about one or more axes in space.

As mentioned, a liquid film is formed on the surface of the template. The liquid film is formed when the template and the mixture comprising the culture medium and the microorganism are moved relative to each other and are thereby brought into contact.

In one embodiment contacting the surface of a template with the mixture is done such that the template is dipped into in the mixture comprising the culture medium and the microorganism. Movement, particularly rotation, of the template in one or more of spatial axes can be superimposed to the immersion an interruption of the contact of the template to mixture.

The oxygen-containing atmosphere is preferably air or pure oxygen or an oxygen-containing gas mixture. Microbial cellulose is formed in and/or on the liquid film when it comes into contact with oxygen.

Separation of Template and Tube:

For use in the implant of the invention, the tube, formed of nanocellulose, is separated from the template.

The separation takes place for example in that the cellulose formed is stripped from the template, or the template is removed in another manner. For example, the cellulose is stripped from a cylindrical template and the tube is obtained.

The template may be rotated, about one or more spatial axes, at least during step c) and/or step f), or one or more of the steps f), when the step f) is carried out several times. With this measure, the shape and distribution of the liquid film and the shape of the forming product can be influenced. In other words, the template is coated with a defined liquid film, which in turn leads to a defined shape of the forming product. The rotation can be done during step a) and b) and/or during the steps d) and e).

This sequence of steps d)-f) are repeated one or more times until a desired amount of cellulose is formed on the surface of the template and the cellulose has reached a desired overall layer thickness. The so-called total layer may be composed of several individual layers or phases. A synthesis of other microbial cellulose takes place on already formed cellulose.

The times of contacting the surface of a template (step a) with a mixture reservoir and of contacting the microbial cellulose generated in step c) with the mixture stock (step d) are referred to as "wetting time". The time of contacting of the liquid film with an oxygen-containing atmosphere (steps c and f) are referred to as "residence time". Wetting times and residence times can be controlled independently of each other. The residence time is in one embodiment, 1-60 minutes, preferably 5-40 min.

The total cultivation time is preferably 1-7 days. The total cultivation time corresponds to the total process time within which all steps of the method are performed, such as turning, wetting and other steps. The duration of the procedure determines the thickness of the formed microbial cellulose on the template, which corresponds to the wall thickness of the tube.

The tube produced by the method can be cleaned to remove residues and components of the culture medium and microorganisms. For cleaning, water, aqueous acidic or alkaline solution or an organic solvent, or a combination, can be used.

The tubes obtained with the method can be used without drying after a cleaning and sterilization process for producing an implant of the invention.

Following description relates to the structure of the microbial cellulose tube.

In the tube, preferably at least the outer surface or the outer layer of the microbial cellulose tube is porous. Porosity can be reached by producing the tube according to above-described method. Porosity improved formation/generation of tissue on the microbial cellulose.

In particular, the tube has a wall with an inner surface and an outer surface, wherein the inner surface and outer surface have an identical or similar cover by fibers of microbial cellulose per unit area. As mentioned, BNC form fibers of more or less dense and more or less porous networks. With methods of image analysis it is possible to distinguish surface areas where there are fibers (in an SEM image, for example, light) from surface areas where are no fibers (gaps, in an SEM image, for example, darker) and to set such areas in relation to the total area.

The coverage per unit area can then be expressed as coverage=part of area section which is covered with fiber/total area of area section The coverage can be expressed as a percentage.

The term "similar" in this context means that coverage the inner surface and the outer surface differ relative to one another by a maximum of 20%, preferably at most 10%, most preferably at most 5%.

The percentage of the difference between the values is calculated as follows:

difference (%)=(number of larger value−number of smaller value)/number of smaller value×100

A similar coverage as defined above represents a similar porosity of the inner and outer surface, wherein the porosity with respect to a surface is two-dimensionally defined as porosity (two-dimensional)=Part of the observed area section not covered with fibers/total area of the area section.

The area not covered with fibers may be referred to as "open-pore surface" or "surface pores".

For the connection between coverage and two-dimensional porosity applies:

Porosity+coverage=1, or expressed as a percentage: porosity (%)+coverage (%)=100%.

In the coverage and porosity BNC fibers can be taken into account, which are just outside of the assumed two-dimensional inner/outer surface. In an electron micrograph a two-dimensional representation of the outer or inner surface of the wall of the hollow body is obtained. The pictured BNC fibers, however, are not always but in a plane, because the surfaces can exhibit a certain roughness and/or optionally BNC fibers imaged are lying out of sight of the viewer behind the surface. It has been found that in the hollow body according to the invention the outer surface of the wall may be rougher than the inner surface. In determining the coverage and porosity preferably all BNC fibers are also taken into account that on a scanning electron micrograph (10,000 times magnification) are visible and they are treated as if they were in a plane, since the coverage/porosity is based on a on a unit area.

Thus, the tube has a wall with an inner surface and an outer surface, the inner surface and the outer surface having a similar porosity, as defined above.

The term "similar" means with respect to the porosity, that the two-dimensional porosity of the inner surface and the outer surface differ relative to one another by a maximum of 20%, preferably at most 10%, most preferably at most 5%.

The percentage of the difference between the values is calculated as follows:

difference (%)=(number of larger value−number of smaller value)/number of smaller value×100th.

The tube has a wall with an inner surface and an outer surface, wherein the wall comprises multiple layers of microbial cellulose, which run parallel to the inner and outer surface of the wall. These layers are hereinafter also referred to as "phases". The layers correspond to the above "single layers or phases" of the wall of the hollow body.

Preferably, the phases are in their density over the entire thickness homogeneous, i.e. they have no density gradient.

The phases are preferably characterized by a uniform (isotropic), well-branched fiber network. Number and strength of the phases are controlled adjustable.

These phases do not have to be obtained by one single process cycle of wetting/filming and subsequent cellulose formation in or on the film. A phase can be formed by several such cycles. The phases are visually distinguishable from each other by scanning electron microscopy, for example, at 24× magnification. The phases are made up of a network of fibers bacterial Nanocellulose, wherein the fiber structures of the phases in the comparison of the phases may be the same or different.

The invention also describes a tube whose wall is made of layers, also referred as phases as described above, wherein one of the layers comprises the inner surface, i.e. the cavity side surface, and a further layer comprises the outer surface, wherein these two layers have an identical or similar porosity. The layer/phase comprising the inner surface of the wall is also referred to as the "lumen-side layer/phase" or "cavity-side layer/phase". The layer/phase comprising the outer surface of the wall is also referred to as "outer-side layer/phase".

With respect to the spatially formed layers/phases, the porosity is spatially defined as: porosity (spatial, three-dimensional)=void volume/total volume In the total volume, the volume of the entire layer/phase may be used. But it is also possible to look at just a fraction of the volume of the layer/phase and look at this volume part to the purpose of measuring the porosity as "total". The term "similar" means with respect to the spatial porosity that the porosity of the lumen-side phase, and the porosity of the outside phase vary relative to each other by at most 20%, preferably at most 10%, most preferably at most 5%.

The percentage of the difference between the values is calculated as follows:

difference (%)=(number of larger value−number of smaller value)/number of smaller value×100th An identical or similar three-dimensional porosity means that the lumen-side layer/phase and the outside layer/phase have an identical or similar density.

Identical or similar three-dimensional porosity, as defined above, means that the lumen-side layer/phase and the outside layer/phase have an identical or similar fiber density.

The density is preferably given as mass/volume and the fiber density is specified as a number of fibers/volume.

For the volume the volume of the entire layer/phase may be used.

However, it is also possible and preferable to consider only a part of the volume of the layer/phase for determining the density or the fiber density.

The term "similar" means with respect to the density and fiber density that the density/fiber density of the lumen-side phase and the density/fiber density of the outside phase relative to each other differ by not more than 20%, preferably at most 10%, most preferably 5% in maximum.

The percentage of the difference between the values is calculated as follows:

difference (%)=(number of larger value−number of smaller value)/number of smaller value×100th Preferably, one or more other phases are disposed between the lumen-side phase and the outside phase. Particularly preferably, these one or more further phases have an identical or similar porosity, density, and fiber density as that of the lumen-side phase and the outside phase.

In a further aspect, the invention is directed to a process for producing a medical implant, comprising:

producing a microbial cellulose tube, comprising
a) contacting the surface of a template which is a negative mold of a cavity of the microbial cellulose tube and of the inner walls of the cavity, with a stock mixture comprising a liquid culture medium and a cellulose-producing microorganism,
b) interrupting of the contact between the template and the stock mixture, wherein on the surface of the template, a liquid film remains comprising the liquid culture medium and the microorganism
c) contacting of the liquid film with an oxygen-containing atmosphere and formation of microbial cellulose in and/or on the liquid film,
d) contacting the microbial cellulose obtained in step c) with the stock mixture,
e) interrupting the contact between the microbial cellulose and the stock mixture wherein on the surface of the microbial cellulose is a film of liquid is left, which comprises the liquid culture medium and the microorganism,
f) contacting the liquid film with an oxygen-containing atmosphere and formation of microbial cellulose in and/or on the liquid film, wherein the sequence of steps d), e) and f) is repeated one or more times,
g) separating the microbial cellulose from the template, introducing a stent, preferably a tubular stent, into the microbial cellulose tube.

With such method, any implant as described before can be produced. The method step of producing a microbial cellulose tube, comprising sub-steps a)-g) have been described before.

Introducing a stent into the tube can be done by sliding the stent into the interior/cavity of the tube.

The implant of the invention can be used for surgery or a method of surgery. The implant can be used for surgery of gall bladder, hepatobiliary malignancy surgery, bile duct and/or liver, e.g. gall removal or liver transplantation. The implant can particularly be used for repairing or regeneration of bile duct. Further fields of use are the use as esophagus implant or urether implant, particularly in case of esophagus or urether lesion.

So, the present invention is also related to a medical implant as described herein, for use in surgery, or in a method of surgery, of gall bladder, hepatobiliary malignancy surgery, bile duct, esophagus, urether or liver.

So, the present invention is also related to a medical implant as described herein, for use in repairing or regeneration, or in a method of repairing or regeneration, of a bile duct, an esophagus lesion or an urether lesion.

The invention will now be described with reference to examples.

A) DESCRIPTION OF THE FIGURES

Figure 2:
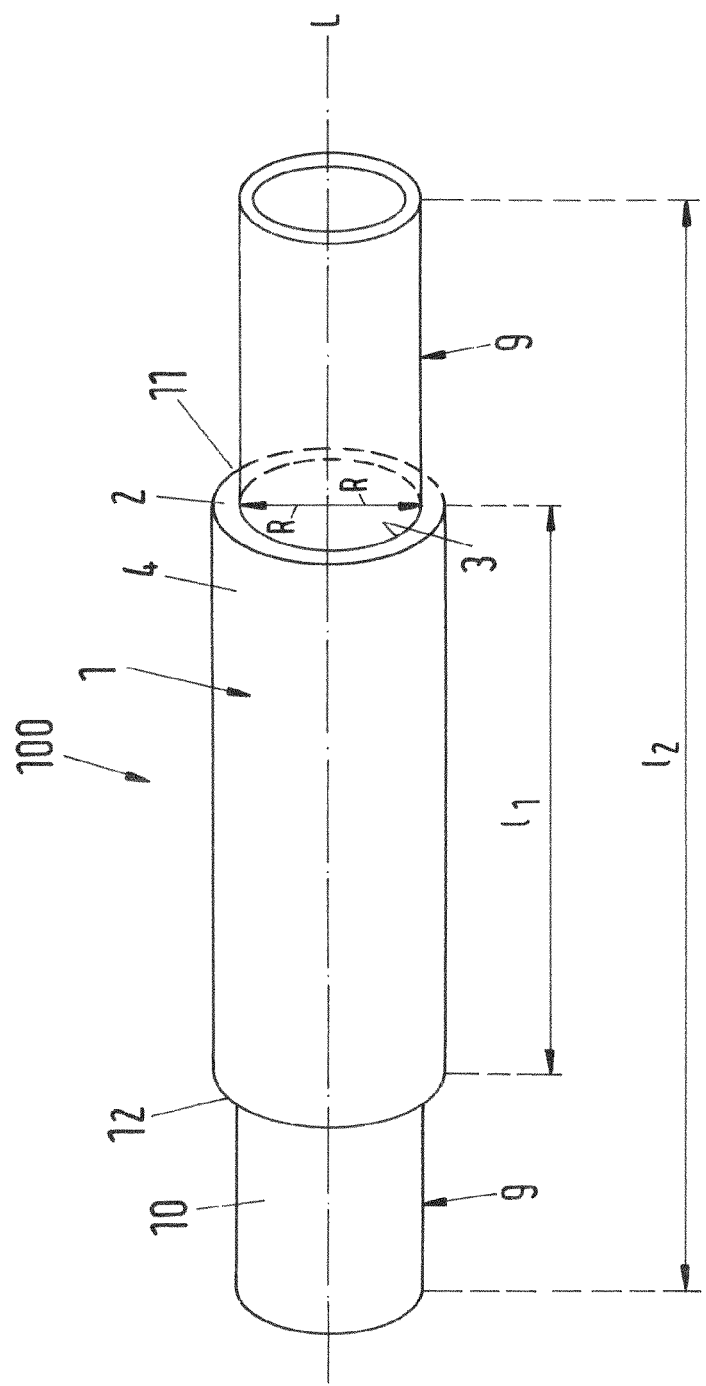
Figure 3:
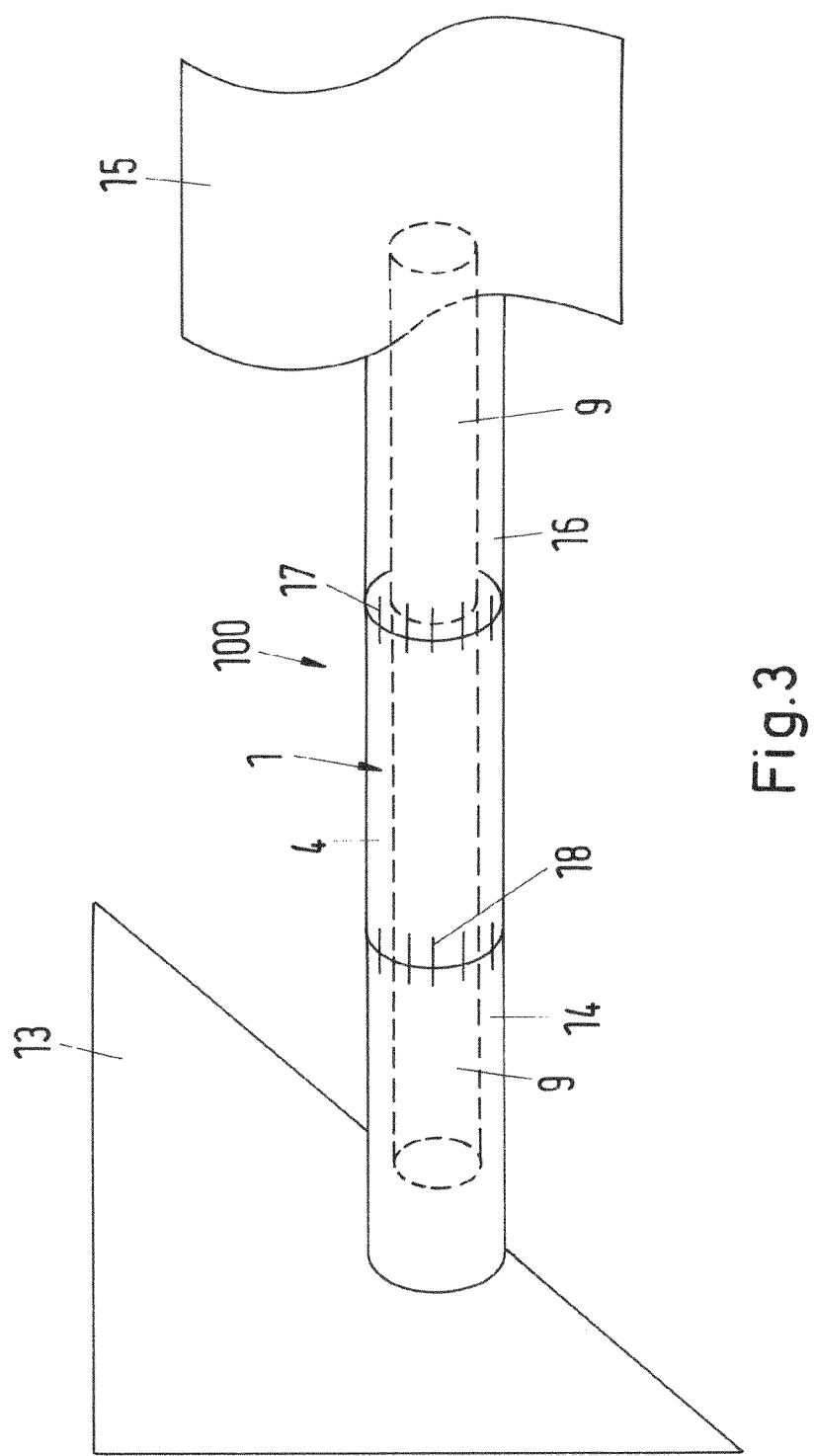

FIG. 1 BNC tube on a template, in a cross section
FIG. 2 A medical implant of the invention
FIG. 3 A medical implant of the invention which is inserted into an animal's body in order to regenerate a bile duct

B) EXAMPLE 1: PREPARATION OF AN IMPLANT a) Preparation of BNC Tube:

A device and reactor as shown and described in FIG. 1 of WO2013/113675A1 is used for preparation of a BNC tube. To prepare the products, several rod shaped templates are arranged in a clamping and inserted into the moving means of the device. The reactor is then closed and sterilized. After sterilization of the entire reactor the reservoir of the reactor is filled under sterile conditions with a mixture of cellulose producing microorganisms and separately sterilized culture solution filled.

Then, the engine of the device is started, and following steps performed:
dipping the templates into the mixture of cellulose producing microorganisms and culture solution in the reservoir, thereby contacting the surface of the templates
removing the templates from the reservoir, thereby interrupting of the contact between the template and the mixture, wherein on the surface of the template, a liquid film remains comprising the liquid culture medium and the microorganism
contacting of the liquid films on templates with the oxygen-containing atmosphere inside of the device and formation of microbial cellulose in and/or on the liquid film. In this step, the templates are rotated around at least two rotational axes, in order to reach a defined and preferably equal distribution of the film The above sequence of steps is repeated several times until the BNC tube on the template has assumed a desired shape a desired wall thickness of about 1-3 mm. The length and inner diameter of each BNC tube is determined by the dimensions of the corresponding rod-shaped template.

At the end of the process, the tubes are stripped from the templates, purified and stored wet, preferably in deionized water.

The BNC tube had a length of approximately 80-150 mm, an inner diameter of approximately 2-4 mm and an outer diameter of approximately 4-10 mm. The number of distinct BNC layers in the tube is about 5-7.

An obtained BNC-tube 1 is shown in a cross section in FIG. 1. The BNC tube 1 is placed onto the template 8, which is a metal rod. L is the longitudinal axis of the BNC tube 1. L extends in the viewing direction. The BNC tube 1 is composed of three layers 5, 6, 7, wherein layer 5 is an inner layer, 6 a middle layer and 7 the outer layer. More than the shown layer 6 between the outer layer 7 and the inner layer 5 can be present. The layers 5, 6, 7 are concentric or substantially concentric to a longitudinal axis (L) of the tube 1. The inner surface of the lumen of the BNC tube 1 is designated as 3, and the outer surface is 4.

An exemplary layer structure in a Scanning electron micrograph is shown in FIG. 3 of WO2013/113675A1.

The layers 5, 6, 7 of microbial cellulose are made of fibers. Exemplary structures are shown in FIGS. 4, 5, and 6 of WO2013/113675A1.

b) Combining BNC Tube and Stent

A biliary stent (8.5 Fr Biliary Drainage Tube Set/Olympus, Tokyo, Japan) with a length of 50-120 mm, a diameter of 8.5 Fr was slit into the tube until the stent protruded both ends of the BNC tube in symmetrical manner.

The obtained implant 100 is shown in appended FIG. 2.

The microbial cellulose tube 1 comprises a wall 2 with the inner surface 3 and the outer surface 4. The wall 2 is composed of the BNC layers 5, 6, 7 that are shown in FIG. 1.

The tubular stent 9 is placed inside of the microbial cellulose tube 1. The outer surface 10 of the stent contacts the inner surface 3 of the microbial cellulose tube 1.

As shown in FIG. 2, the length 12 of the stent 9 is longer than the length $l_1$ of the BNC tube 1. The tubular stent 9 protrudes from the microbial cellulose tube at a first end 11 of the microbial cellulose tube 1 and a second end 12 of the microbial cellulose tube 1.

In the example of FIG. 2, the outer diameter of the stent 9 may be higher than the inner diameter of the BNC tube 1 (without stent 9). In this case, the tube 1 is expanded in radial direction. Exemplary directions of expansion are designated with arrows R. It is to be understood that expansion will in this example occur also in other radial directions, since the stent 9 and the tube 1 are circular. A more or less symmetric expansion occurs, thereby increasing the inner diameter of the tube 1.

C) EXAMPLE 2: INSERTION OF THE IMPLANT INTO ANIMAL TO REGENERATE A BILE DUCT

Comparative example: In a first experiment, only a BNC tube, without stent, was used as an implant. Implantation was done after resection of a bile duct segment in a pig, having a length of 3 cm. The BNC tube was interposed after length adjustment in end-to-end manner using 6/0-Prolene sutures.

In a second experiment an implant as shown in FIG. 2 was used. FIG. 3 shows the implant 100 in a pig in a schematic view. Reference signs correspond to reference signs in FIG. 2, as far as the implant 100 is concerned.

FIG. 3 shows a part of a pig's liver 13 with a first bile duct section, or bile duct end, 14 and a part of the duodenum 15 with a second bile duct section, or bile duct end, 16. In the first bile duct section 14, a first protruding part of the stent 9 was introduced. In the second bile duct section 16, a second protruding part of the stent 9 was introduced. The BNC tube 1 is placed between the bile duct sections 14, 16. A connection between the BNC tube 1 and the bile duct sections 14, 16 is made by sutures 17, 18.

After insertion of the implant 100 in a pig as shown in FIG. 3 the implant 100 was left for four or eight weeks in the animal. Following results were obtained:

The BNC tube was still placed in the bile duct, i.e. between the bile duct sections 14, 16 but was not grown together with the bile duct sections 14, 16.

New bile duct epithelium was continuously formed on the surface 4 of the BNC tube, as shown by histologic analysis. In result, the bile duct sections 14, 16 were connected by new bile duct epithelium. The anastomosis was sufficient, in a sense that an anastomosis ring could be observed. No badly healed or insufficient anastomosis were observed. The actual anastomosis was not existent any more since the interponate, i.e. the BNC tube, was repelled.

The implant 100, i.e. the BNC tube 1 and the stent 4 could be removed from the bile duct sections 14, 16 and the newly created bile duct epithelium. The stent 9 was removed through the duodenum 15. Thereby, the BNC tube 1 was also removed. The BNC tube 1 disassociated from the new bile duct epithelium which was grown on its surface.

What is claimed is:

1. A method for producing a medical implant, comprising: providing a microbial cellulose tube, comprising a wall having an inner surface and an outer surface, wherein the wall comprises several layers of microbial cellulose, wherein said layers are concentric to a longitudinal axis of the tube; and introducing a stent into the microbial cellulose tube to form the medical implant.

2. A method according to claim 1 comprising the steps of: producing the microbial cellulose tube by:
   a) contacting the surface of a template which is a negative mold of a cavity of the microbial cellulose tube and of the inner walls of the cavity, with a stock mixture comprising a liquid culture medium and a cellulose-producing microorganism;
   b) interrupting of the contact between the template and the stock mixture, wherein on the surface of the template, a liquid film remains comprising the liquid culture medium and the microorganism;
   c) contacting of the liquid film with an oxygen-containing atmosphere and forming microbial cellulose in and/or on the liquid film;
   d) contacting the microbial cellulose obtained in step c) with the stock mixture,
   e) interrupting the contact between the microbial cellulose and the stock mixture wherein on the surface of the microbial cellulose is a film of liquid is left, which comprises the liquid culture medium and the microorganism;
   f) contacting the liquid film with an oxygen-containing atmosphere and forming microbial cellulose in and/or on the liquid film; wherein the sequence of steps d), e) and f) is repeated one or more times;
   g) separating the microbial cellulose from the template to obtain the tube.

3. A method according to claim 1, further comprising expanding the microbial cellulose tube in a radial direction by inserting the tubular stent into the microbial cellulose tube.

4. A method according to claim 3, wherein the outer diameter of the stent before introducing the stent into the microbial cellulose tube is higher than the inner diameter of the microbial cellulose tube so that the microbial cellulose tube is expanded in one or more radial directions by the stent when the stent is introduced into the microbial cellulose tube.

5. A method according to claim 1, wherein the microbial cellulose tube is expanded by the stent in one or more radial directions (R).

6. A method according to claim 5, wherein the stent is removable from the cellulose tube, further comprising removing the stent from the cellulose tube.

7. A method according to claim 1, wherein the stent is introduced such that an outer surface of the stent contacts the inner surface of the microbial cellulose tube.

8. A method according to claim 1, further comprising rotating the template having the liquid film around at least two rotational axes to equally distribute the film on the template and form the tube.

9. A method according to claim 1, further comprising stripping the tube from the template when separating the microbial cellulose from the template.

10. A method according to claim 1, further comprising purifying the tube.

11. A method according to claim 1, further comprising storing the tube in deionized water.

12. A method according to claim 1, further comprising inserting the stent such that it protrudes from both ends of the tube.

13. A method according to claim 1, wherein the template is a metal rod.

14. A method according to claim 3, wherein by the expansion, at least an outer layer of the tube is subjected to a compaction.

15. A method according to claim 3, wherein by the expansion a porosity of at least an outer layer of the tube is decreased.

16. A method according to claim 3, wherein the tube is radially expanded over its whole length.

17. A method according to claim 1, wherein the stent is a tubular stent.

18. A method according to claim 1, wherein the stent is introduced into the microbial cellulose tube by sliding into an interior of the tube.

19. A method according to claim 17, wherein the tubular stent has a closed jacket.

20. A method according to claim 1, wherein the layers of microbial cellulose are made of fibers.

21. A method according to claim 1, wherein the stent is a biliary stent, a urinary stent or a stent for an esophagus.

22. A method according to claim 1, wherein the stent is made of a polymer.

23. A method for producing a medical implant, comprising:
producing a microbial cellulose tube by:
a) contacting the surface of a template which is a negative mold of a cavity of the microbial cellulose tube and of the inner walls of the cavity, with a stock mixture comprising a liquid culture medium and a cellulose-producing microorganism;
b) interrupting of the contact between the template and the stock mixture, wherein on the surface of the template, a liquid film remains comprising the liquid culture medium and the microorganism;
c) contacting of the liquid film with an oxygen-containing atmosphere and formation of microbial cellulose in and/or on the liquid film;
d) contacting the microbial cellulose obtained in step c) with the stock mixture,
e) interrupting the contact between the microbial cellulose and the stock mixture wherein on the surface of the microbial cellulose is a film of liquid is left, which comprises the liquid culture medium and the microorganism;
f) contacting the liquid film with an oxygen-containing atmosphere and formation of microbial cellulose in and/or on the liquid film;
wherein the sequence of steps d), e) and f) is repeated one or more times;
g) separating the microbial cellulose from the template; and introducing a stent into the microbial cellulose tube to form the medical implant.

24. A method comprising providing a microbial cellulose tube, comprising a wall having an inner surface and an outer surface, wherein the wall comprises several layers of microbial cellulose, wherein said layers are concentric to a longitudinal axis of the tube;
introducing a stent into the microbial cellulose tube to form the medical implant; and implanting the medical implant in a subject.

25. A method for producing a medical implant, comprising:
providing a microbial cellulose tube, comprising a wall having an inner surface and an outer surface, wherein the wall comprises several layers of microbial cellulose, wherein said layers are concentric to a longitudinal axis of the tube; and introducing a stent into the microbial cellulose tube to form the medical implant;
further comprising expanding the microbial cellulose tube in a radial direction by inserting the tubular stent into the microbial cellulose tube;
wherein the outer diameter of the stent before introducing the stent into the microbial cellulose tube is higher than the inner diameter of the microbial cellulose tube so that the microbial cellulose tube is expanded in one or more radial directions by the stent when the stent is introduced into the microbial cellulose tube; and
wherein the stent is introduced into the microbial cellulose tube by sliding into an interior of the tube.

* * * * *